United States Patent
Miyake et al.

(10) Patent No.: US 7,125,704 B2
(45) Date of Patent: Oct. 24, 2006

(54) GLUCONATE DEHYDRATASE

(75) Inventors: Hitoki Miyake, Chiba (JP); Toshifumi Yamaki, Chiba (JP); Toshihiro Oikawa, Chiba (JP); Takeshi Nakamura, Kanagawa (JP); Hiroki Ishibashi, Fukuoka (JP); Yasushi Fukuiri, Fukuoka (JP); Atsushi Sakuma, Fukuoka (JP); Hironori Komatsu, Chiba (JP); Tomoyuki Ando, Chiba (JP); Kazuhiko Togashi, Chiba (JP); Hideki Umetani, Chiba (JP)

(73) Assignee: Mitsui Chemicals, Inc., Tokyo (JP)

( * ) Notice: Subject to any disclaimer, the term of this patent is extended or adjusted under 35 U.S.C. 154(b) by 83 days.

(21) Appl. No.: 10/885,874

(22) Filed: Jul. 8, 2004

(65) Prior Publication Data

US 2005/0054042 A1    Mar. 10, 2005

(30) Foreign Application Priority Data

Jul. 10, 2003   (JP)   ............... 2003-194680

(51) Int. Cl.
*C12N 9/88*   (2006.01)
*C12P 7/40*   (2006.01)
*C12P 7/58*   (2006.01)
*C12P 21/06*  (2006.01)

(52) U.S. Cl. ............... 435/232; 435/136; 435/137; 435/69.1

(58) Field of Classification Search ............... 435/232, 435/136, 137, 69.1
See application file for complete search history.

(56) References Cited

U.S. PATENT DOCUMENTS 6,562,958 B1 *  5/2003  Breton et al. .............. 536/23.7

OTHER PUBLICATIONS

Kersters et al (and properties of D-gluconate dehydratase from Achromobacter. Antonie Van Leewenhoek 37 (1971) 233-246.*
R. Bender et al., "Enzymatic Synthesis of 2-Keto-3-deoxy-D-gluconate from D-Gluconate," *Analytical Biochemistry*, 1974, pp. 275-279, vol. 61, Academic Press, Inc.
K. Kersters et al., "2-Keto-3-deoxy-D-gluconate," *Methods of Enzymology*, 1975, pp. 99-101, vol. 41.
B. Nicolaus et al., "Production of 2-Keto-3-Deoxygluconate by Immobilized Cells of Sulfolobus Solfataricus," *Biotechnology Letters*, 1986, pp. 497-500, vol. 8, No. 7.

* cited by examiner

*Primary Examiner*—Rebecca E. Prouty
*Assistant Examiner*—Kagnew Gebreyesus
(74) *Attorney, Agent, or Firm*—Buchanan Ingersoll & Rooney PC

(57) ABSTRACT

A novel gluconate dehydratase derived from *Achromobacter xylosoxidans* and a gene encoding the gluconate dehydratase are provided. By reacting the gluconate dehydratase or a transformed cell containing the gene with an aldonic acid, the corresponding 2-keto-3-deoxyaldonic acid can be efficiently produced.

2 Claims, 1 Drawing Sheet

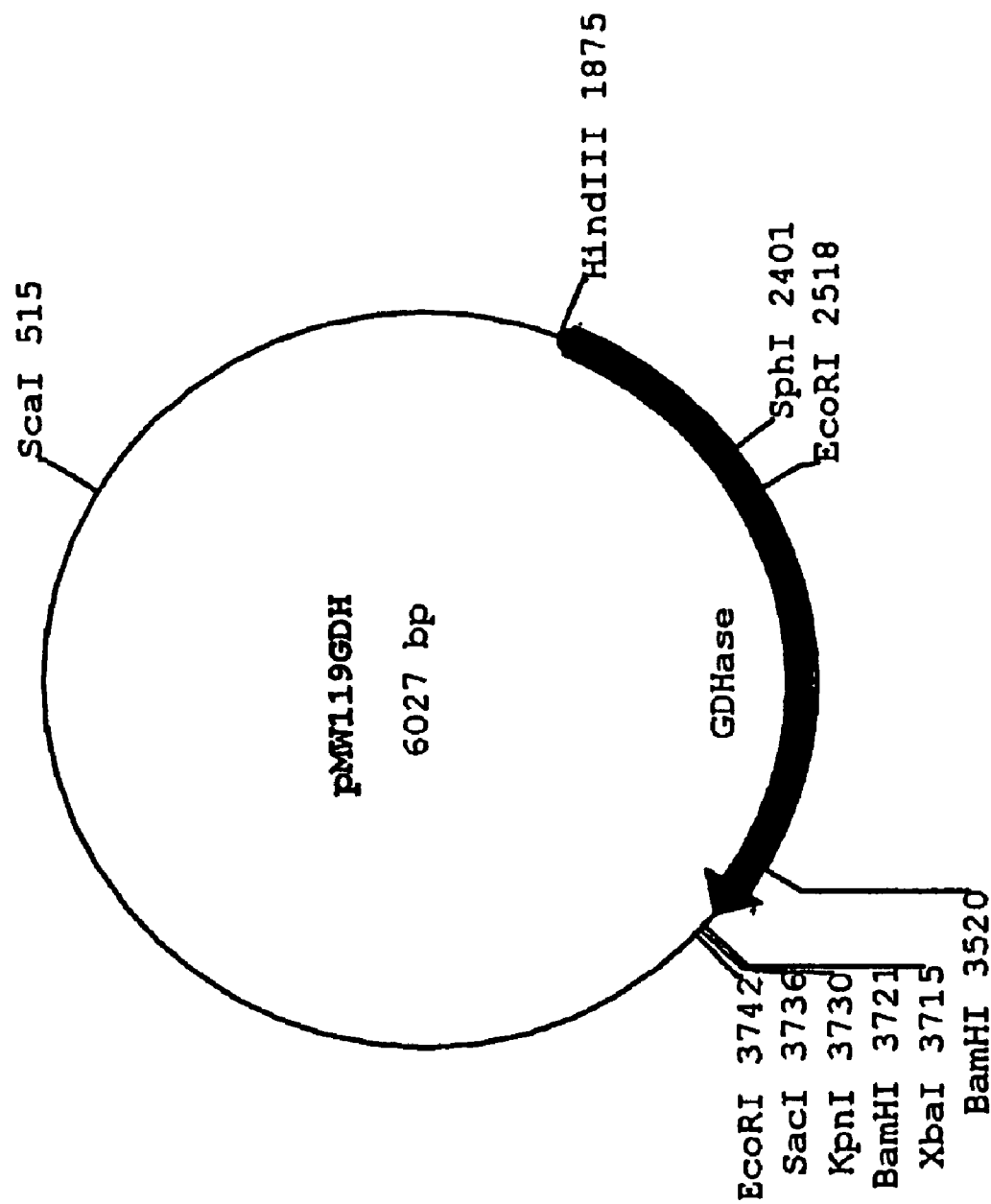

SEQUENCE LISTING

```
<160> NUMBER OF SEQ ID NOS: 8

<210> SEQ ID NO 1
<211> LENGTH: 1782
<212> TYPE: DNA
<213> ORGANISM: Achromobacter xylosoxidans
<220> FEATURE:
<221> NAME/KEY: CDS
<222> LOCATION: (1)...(1779)
<223> OTHER INFORMATION: gene="D-gluconic acid dehydratase"
      product="D-gluconic acid dehydratase"
```

<400> SEQUENCE: 1

```
atg acc gac act ccc cgc aag ctg cgc agc cag aaa tgg ttc gac gat    48
Met Thr Asp Thr Pro Arg Lys Leu Arg Ser Gln Lys Trp Phe Asp Asp
 1               5                  10                  15 ccc gcc cac gcc gac atg acg gcg atc tac gtc gag cgc tac ctg aac    96
Pro Ala His Ala Asp Met Thr Ala Ile Tyr Val Glu Arg Tyr Leu Asn
             20                  25                  30 tac ggc ctg acg cgc cag gaa ctg caa tcg ggc cgg ccc atc atc ggc   144
Tyr Gly Leu Thr Arg Gln Glu Leu Gln Ser Gly Arg Pro Ile Ile Gly
         35                  40                  45 atc gcc cag acc ggc agc gac ctg gcg ccc tgc aac cgc cac cac ctg   192
Ile Ala Gln Thr Gly Ser Asp Leu Ala Pro Cys Asn Arg His His Leu
 50                  55                  60 gcg ctg gcc gaa cgc atc aag gcc ggc atc cgc gac gcc ggc ggc atc   240
Ala Leu Ala Glu Arg Ile Lys Ala Gly Ile Arg Asp Ala Gly Gly Ile
 65                  70                  75                  80 ccg atg gag ttc ccg gtg cat ccg ctg gcc gag cag ggc cgc cgc ccg   288
Pro Met Glu Phe Pro Val His Pro Leu Ala Glu Gln Gly Arg Arg Pro
             85                  90                  95 acc gcg gcg ctg gac cgc aac ctg gcc tac ctg ggc ctg gtg gag atc   336
Thr Ala Ala Leu Asp Arg Asn Leu Ala Tyr Leu Gly Leu Val Glu Ile
            100                 105                 110 ctg cac ggc tat ccg ctg gac ggc gtg gtg ctg acc acg ggc tgc gac   384
Leu His Gly Tyr Pro Leu Asp Gly Val Val Leu Thr Thr Gly Cys Asp
        115                 120                 125 aag acc acg ccc gcc tgc ctg atg gcg gcg gcc acc gtc gac att ccc   432
Lys Thr Thr Pro Ala Cys Leu Met Ala Ala Ala Thr Val Asp Ile Pro
130                 135                 140 gcc atc gtg ctg tcc ggc ggc ccg atg ctg gac ggc tgg cat gac ggc   480
Ala Ile Val Leu Ser Gly Gly Pro Met Leu Asp Gly Trp His Asp Gly
145                 150                 155                 160 cag cgc gtc ggg tcc ggc acg gtc atc tgg cat gcc cgc aac ctg atg   528
Gln Arg Val Gly Ser Gly Thr Val Ile Trp His Ala Arg Asn Leu Met
            165                 170                 175 gcc gcg ggc aag ctg gac tac gaa ggc ttc atg acg ctg gcc acc gcc   576
Ala Ala Gly Lys Leu Asp Tyr Glu Gly Phe Met Thr Leu Ala Thr Ala
        180                 185                 190 tcc tcg ccc tcg atc ggc cac tgc aac acc atg ggc acg gcg ctg tcc   624
Ser Ser Pro Ser Ile Gly His Cys Asn Thr Met Gly Thr Ala Leu Ser
    195                 200                 205 atg aat tcg ctg gcc gag gcg ctg ggc atg tcg ctg ccc acc tgc gcc   672
Met Asn Ser Leu Ala Glu Ala Leu Gly Met Ser Leu Pro Thr Cys Ala
210                 215                 220 agc atc ccc gcg ccc tac cgc gaa cgc ggg cag atg gcc tac gcc acc   720
Ser Ile Pro Ala Pro Tyr Arg Glu Arg Gly Gln Met Ala Tyr Ala Thr
225                 230                 235                 240 ggc ctg cgc atc tgc gac atg gtg cgc gag gac ctg cgc ccg tcc cgc   768
Gly Leu Arg Ile Cys Asp Met Val Arg Glu Asp Leu Arg Pro Ser Arg
            245                 250                 255 atc ctg acg cgc gag gcc ttc gaa aac gcc atc gtc gtg gcc tcg gcg   816
Ile Leu Thr Arg Glu Ala Phe Glu Asn Ala Ile Val Val Ala Ser Ala
        260                 265                 270 ctg ggc gcg tcc agc aac tgt ccg ccg cac ctg atc gcc atg gcg cgc   864
Leu Gly Ala Ser Ser Asn Cys Pro Pro His Leu Ile Ala Met Ala Arg
    275                 280                 285 cat gcc ggc atc gac ctg agc ctg gac gac tgg cag cgg ctg ggc gaa   912
His Ala Gly Ile Asp Leu Ser Leu Asp Asp Trp Gln Arg Leu Gly Glu
290                 295                 300
```

```
gac gtg ccg ctg ctg gtg aac tgc gtg ccc gcc ggc gaa cac ctg ggc    960
Asp Val Pro Leu Leu Val Asn Cys Val Pro Ala Gly Glu His Leu Gly
305                 310                 315                 320 gag ggc ttc cac cgc gcc ggc ggc gtg ccg gcc gtg atg cac gaa ctg   1008
Glu Gly Phe His Arg Ala Gly Gly Val Pro Ala Val Met His Glu Leu
                325                 330                 335 ctg gcc gcc ggc cgc ctg cac gcc gac tgc gcc acc gtg tcc ggc aag   1056
Leu Ala Ala Gly Arg Leu His Ala Asp Cys Ala Thr Val Ser Gly Lys
            340                 345                 350 acc atc ggc gaa atc gcg gcc ggc gcc aag acc cac gac gcc gac gtc   1104
Thr Ile Gly Glu Ile Ala Ala Gly Ala Lys Thr His Asp Ala Asp Val
        355                 360                 365 atc cgc ggc tgc gac gcg ccg ctc aag cac cgc gcc ggc ttc atc gtg   1152
Ile Arg Gly Cys Asp Ala Pro Leu Lys His Arg Ala Gly Phe Ile Val
    370                 375                 380 ctg tcg ggc aat ttc ttc gac agc gcg gtc atc aag atg tcg gtg gtg   1200
Leu Ser Gly Asn Phe Phe Asp Ser Ala Val Ile Lys Met Ser Val Val
385                 390                 395                 400 ggc gag gcg ttc cgc cgc gcc tac ctg tcc gcg ccc ggc gac gag aat   1248
Gly Glu Ala Phe Arg Arg Ala Tyr Leu Ser Ala Pro Gly Asp Glu Asn
                405                 410                 415 gcc ttc gag gcc cgg gcc atc gtg ttc gaa gga ccg gag gac tac cac   1296
Ala Phe Glu Ala Arg Ala Ile Val Phe Glu Gly Pro Glu Asp Tyr His
            420                 425                 430 gcg cgc atc gaa gac ccg gcc ctg aac atc gac gaa cac tgc atc ctg   1344
Ala Arg Ile Glu Asp Pro Ala Leu Asn Ile Asp Glu His Cys Ile Leu
        435                 440                 445 gtc atc cgc ggc gcc ggc acg gtc ggc tat ccg ggc agc gcc gag gtc   1392
Val Ile Arg Gly Ala Gly Thr Val Gly Tyr Pro Gly Ser Ala Glu Val
    450                 455                 460 gtc aac atg gcg ccg cca tcg cac ctg atc aag cgc ggc atc gac tcg   1440
Val Asn Met Ala Pro Pro Ser His Leu Ile Lys Arg Gly Ile Asp Ser
465                 470                 475                 480 ctg ccc tgc ctg ggc gac ggc cgc cag agc ggc acc tcg gcc agt ccg   1488
Leu Pro Cys Leu Gly Asp Gly Arg Gln Ser Gly Thr Ser Ala Ser Pro
                485                 490                 495 tcg atc ctg aac atg tcg cca gaa gcc gcc gtg ggt ggc ggt ctg gcg   1536
Ser Ile Leu Asn Met Ser Pro Glu Ala Ala Val Gly Gly Gly Leu Ala
            500                 505                 510 ctg ctg cgc acc ggc gac cgc atc cgc gtc gac ctg aac cag cgc agc   1584
Leu Leu Arg Thr Gly Asp Arg Ile Arg Val Asp Leu Asn Gln Arg Ser
        515                 520                 525 gtc atc gcg ctg gtg gac gaa gcc gaa ctg gcg cgg cgg cgg cag gat   1632
Val Ile Ala Leu Val Asp Glu Ala Glu Leu Ala Arg Arg Arg Gln Asp
    530                 535                 540 ccg ccc tac cag ccg ccg ccg gcc cag acg ccg tgg cag gag ctg tac   1680
Pro Pro Tyr Gln Pro Pro Pro Ala Gln Thr Pro Trp Gln Glu Leu Tyr
545                 550                 555                 560 cgg caa ctg gtc ggc cag ttg tca acc ggc ggc tgc ctg gaa ccc tcc   1728
Arg Gln Leu Val Gly Gln Leu Ser Thr Gly Gly Cys Leu Glu Pro Ser
                565                 570                 575 acc ctg tac ctg aag gtg gtc gaa acg cgc ggt gat ccc cgg cat tcg   1776
Thr Leu Tyr Leu Lys Val Val Glu Thr Arg Gly Asp Pro Arg His Ser
            580                 585                 590 cac tga                                                           1782
His

<210> SEQ ID NO 2
<211> LENGTH: 593
<212> TYPE: PRT
```

<213> ORGANISM: Achromobacter xylosoxidans

<400> SEQUENCE: 2

```
Met Thr Asp Thr Pro Arg Lys Leu Arg Ser Gln Lys Trp Phe Asp Asp
 1               5                  10                  15

Pro Ala His Ala Asp Met Thr Ala Ile Tyr Val Glu Arg Tyr Leu Asn
            20                  25                  30

Tyr Gly Leu Thr Arg Gln Glu Leu Gln Ser Gly Arg Pro Ile Ile Gly
        35                  40                  45

Ile Ala Gln Thr Gly Ser Asp Leu Ala Pro Cys Asn Arg His His Leu
50                  55                  60

Ala Leu Ala Glu Arg Ile Lys Ala Gly Ile Arg Asp Ala Gly Gly Ile
65                  70                  75                  80

Pro Met Glu Phe Pro Val His Pro Leu Ala Glu Gln Gly Arg Arg Pro
                85                  90                  95

Thr Ala Ala Leu Asp Arg Asn Leu Ala Tyr Leu Gly Leu Val Glu Ile
            100                 105                 110

Leu His Gly Tyr Pro Leu Asp Gly Val Val Leu Thr Thr Gly Cys Asp
        115                 120                 125

Lys Thr Thr Pro Ala Cys Leu Met Ala Ala Thr Val Asp Ile Pro
130                 135                 140

Ala Ile Val Leu Ser Gly Gly Pro Met Leu Asp Gly Trp His Asp Gly
145                 150                 155                 160

Gln Arg Val Gly Ser Gly Thr Val Ile Trp His Ala Arg Asn Leu Met
                165                 170                 175

Ala Ala Gly Lys Leu Asp Tyr Glu Gly Phe Met Thr Leu Ala Thr Ala
            180                 185                 190

Ser Ser Pro Ser Ile Gly His Cys Asn Thr Met Gly Thr Ala Leu Ser
        195                 200                 205

Met Asn Ser Leu Ala Glu Ala Leu Gly Met Ser Leu Pro Thr Cys Ala
    210                 215                 220

Ser Ile Pro Ala Pro Tyr Arg Glu Arg Gly Gln Met Ala Tyr Ala Thr
225                 230                 235                 240

Gly Leu Arg Ile Cys Asp Met Val Arg Glu Asp Leu Arg Pro Ser Arg
                245                 250                 255

Ile Leu Thr Arg Glu Ala Phe Glu Asn Ala Ile Val Val Ala Ser Ala
            260                 265                 270

Leu Gly Ala Ser Ser Asn Cys Pro Pro His Leu Ile Ala Met Ala Arg
        275                 280                 285

His Ala Gly Ile Asp Leu Ser Leu Asp Asp Trp Gln Arg Leu Gly Glu
    290                 295                 300

Asp Val Pro Leu Leu Val Asn Cys Val Pro Ala Gly Glu His Leu Gly
305                 310                 315                 320

Glu Gly Phe His Arg Ala Gly Val Pro Ala Val Met His Glu Leu
                325                 330                 335

Leu Ala Ala Gly Arg Leu His Ala Asp Cys Ala Thr Val Ser Gly Lys
            340                 345                 350

Thr Ile Gly Glu Ile Ala Ala Gly Ala Lys Thr His Asp Ala Asp Val
        355                 360                 365

Ile Arg Gly Cys Asp Ala Pro Leu Lys His Arg Ala Gly Phe Ile Val
    370                 375                 380

Leu Ser Gly Asn Phe Phe Asp Ser Ala Val Ile Lys Met Ser Val Val
385                 390                 395                 400
```

```
Gly Glu Ala Phe Arg Arg Ala Tyr Leu Ser Ala Pro Gly Asp Glu Asn
                405                 410                 415
Ala Phe Glu Ala Arg Ala Ile Val Phe Glu Gly Pro Glu Asp Tyr His
            420                 425                 430
Ala Arg Ile Glu Asp Pro Ala Leu Asn Ile Asp Glu His Cys Ile Leu
        435                 440                 445
Val Ile Arg Gly Ala Gly Thr Val Gly Tyr Pro Gly Ser Ala Glu Val
    450                 455                 460
Val Asn Met Ala Pro Ser His Leu Ile Lys Arg Gly Ile Asp Ser
465                 470                 475                 480
Leu Pro Cys Leu Gly Asp Gly Arg Gln Ser Gly Thr Ser Ala Ser Pro
                485                 490                 495
Ser Ile Leu Asn Met Ser Pro Glu Ala Ala Val Gly Gly Leu Ala
                500                 505                 510
Leu Leu Arg Thr Gly Asp Arg Ile Arg Val Asp Leu Asn Gln Arg Ser
            515                 520                 525
Val Ile Ala Leu Val Asp Glu Ala Glu Leu Ala Arg Arg Gln Asp
    530                 535                 540
Pro Pro Tyr Gln Pro Pro Ala Gln Thr Pro Trp Gln Glu Leu Tyr
545                 550                 555                 560
Arg Gln Leu Val Gly Gln Leu Ser Thr Gly Gly Cys Leu Glu Pro Ser
                565                 570                 575
Thr Leu Tyr Leu Lys Val Val Glu Thr Arg Gly Asp Pro Arg His Ser
                580                 585                 590
His

<210> SEQ ID NO 3
<211> LENGTH: 15
<212> TYPE: PRT
<213> ORGANISM: Achromobacter xylosoxidans
<220> FEATURE:
<221> NAME/KEY: PEPTIDE
<222> LOCATION: (1)...(15)
<223> OTHER INFORMATION: N end amino acid arrangement of the fragment of
      D-gluconic acid dehydratase decomposed by
      lysil-end peptidase.

<400> SEQUENCE: 3

Thr Asp Thr Pro Arg Lys Leu Arg Ser Gln Lys Trp Phe Asp Asp
 1               5                  10                  15

<210> SEQ ID NO 4
<211> LENGTH: 15
<212> TYPE: PRT
<213> ORGANISM: Achromobacter xylosoxidans
<220> FEATURE:
<221> NAME/KEY: PEPTIDE
<222> LOCATION: (1)...(15)
<223> OTHER INFORMATION: N end amino acid arrangement of the fragment of
      D-gluconic acid dehydratase decomposed by
      lysil-end peptidase.

<400> SEQUENCE: 4

Ala Arg Ala Ile Val Phe Glu Gly Pro Glu Asp Tyr His Ala Arg
 1               5                  10                  15

<210> SEQ ID NO 5
<211> LENGTH: 44
<212> TYPE: DNA
<213> ORGANISM: Artificial Sequence
<220> FEATURE:
<223> OTHER INFORMATION: Oligonucleotide to act as a PCR primer
```

-continued

```
<220> FEATURE:
<221> NAME/KEY: misc_feature
<222> LOCATION: 3, 9, 21, 24, 27
<223> OTHER INFORMATION: n = A,T,C or G

<400> SEQUENCE: 5
acngayacnc cgcggaaryt nmgnwsncar aartggttyg ayga              44

<210> SEQ ID NO 6
<211> LENGTH: 40
<212> TYPE: DNA
<213> ORGANISM: Artificial Sequence
<220> FEATURE:
<221> NAME/KEY: misc_feature
<222> LOCATION: 20, 23, 32, 38
<223> OTHER INFORMATION: n = A,T,C or G
<220> FEATURE:
<223> OTHER INFORMATION: Oligonucleotide to act as a PCR primer

<400> SEQUENCE: 6
ctcgagcrtg rtartcytcn ggnccytcra anacdatngc                   40

<210> SEQ ID NO 7
<211> LENGTH: 20
<212> TYPE: DNA
<213> ORGANISM: Artificial Sequence
<220> FEATURE:
<223> OTHER INFORMATION: Oligonucleotide to act as a PCR primer

<400> SEQUENCE: 7
ccgaagctta cgaggcaccc                                         20

<210> SEQ ID NO 8
<211> LENGTH: 30
<212> TYPE: DNA
<213> ORGANISM: Artificial Sequence
<220> FEATURE:
<223> OTHER INFORMATION: Oligonucleotide to act as a PCR primer

<400> SEQUENCE: 8
acgcatctag atcctctaca ttgcgggcgt                              30
```

GLUCONATE DEHYDRATASE

BACKGROUND OF THE INVENTION

1. Field of the Invention

The present invention relates to a novel gluconate dehydratase capable of efficiently producing a 2-keto-3-deoxyaldonic acid from aldonic acid, to a base sequence encoding the gluconate dehydratase, to a plasmid containing the base sequence, and to a cell transformed by the plasmid. The present invention also relates to a process with use of the gluconate dehydratase or the transformed cell for producing a 2-keto-3-deoxyaldonic acid and a 2-deoxyaldonic acid or 2-deoxyaldose whose carbon number is reduced by 1.

2. Description of the Related Art 2-keto-3-deoxyaldonic acids are useful as pharmaceutical material. For example, 2-keto-3-deoxyaldonic acids are decarboxylated to 2-deoxyaldonic acids or 2-deoxyaldoses whose carbon number is reduced by 1. These substances are thought of for raw materials of antibiotics, antiviral agents, antisense drugs, and other drugs and medicines.

On the other hand, enzymes have been known which catalyze a reaction for producing 2-keto-3-deoxyaldonic acids by dehydration of aldonic acids. For example, a gluconate dehydratase (EC4. 2. 1. 39) for dehydrating D-gluconic acid to synthesize 2-keto-3-deoxy-D-gluconic acid is derived from *Clostridium pasteurianum* (Analytical Biochemistry 61, 275 (1974)), *Alcaligenes* sp. strain M250 (Methods in Enzymology 41, 99 (1975)), or *Sulfolobus solfataricus* (Biotechnol. Lett. 8,497 (1986)). Unfortunately, it is reported that the gluconate dehydratase derived from *Clostridium pasteurianum* is liable to oxidize with air and is thus rapidly deactivated in the presence of air. The gluconate dehydratase derived from *Alcaligenes* sp. strain M250 is not thermally stable. A report has taught that the dehydration activity of the gluconate dehydratase is 50% degraded in storage at 0° C. for 7 days in a tris(hydroxymethyl)aminomethane (hereinafter referred to as Tris) buffer solution (pH 8.0 to 8.8) containing 1 mM of sodium D-gluconate and 1 mM of magnesium chloride. Hence, these microorganisms or enzymes derived from these microorganisms are not suitable for industrial production because of the difficulty in handling, such as degradation of the reactivity in a process. The gluconate dehydratase derived from *Sulfolobus solfataricus* has not yet purified, and accordingly, its scientific characteristics have not been known. For synthesis of 2-keto-3-deoxy-D-gluconic acid with use of the *Sulfolobus solfataricus* as it is, this microorganism has activity of decomposing the product 2-keto-3-deoxy-D-gluconic acid, thus causing the yield to decrease.

As described above, no gluconate dehydratase industrially applicable in practice has been discovered, and no industrial process for efficiently producing a 2-keto-3-deoxyaldonic acid has been established.

SUMMARY OF THE INVENTION

Accordingly, an object of the present invention is to provide a novel gluconate dehydratase having such a thermostability and storage stability as to be industrially used in practice and capable of efficiently producing a 2-keto-3-deoxyaldonic acid, which is useful for pharmaceutical material, from the corresponding aldonic acid, and to a process for producing a 2-keto-3-deoxyaldonic acid with use of the gluconate dehydratase.

Another object of the present invention is to provide a base sequence encoding the gluconate dehydratase, a plasmid containing the base sequence, and a cell into which a host cell is transformed with the plasmid. The base sequence is advantageously used in productions of the gluconate dehydratase and of 2-keto-3-deoxyaldonic acids using the gluconate dehydratase.

The inventors of the present invention have conducted intensive research to find that *Achromobacter xylosoxidans* strain ATCC 9220 exhibits a high activity of dehydrating gluconic acid.

A paper on the *Alcaligenes* sp. strain M250 said that the strain M250 is the same type as the ATCC 9220 strain, and the gluconate dehydratase derived from *Alcaligenes* sp. strain M250 is reported to be unstable, as described above. However, the inventors found that D-gluconic acid acted upon by *Achromobacter xylosoxidans* strain ATCC 9220 maintains its activity stably even at a reaction temperature of 50° C. and efficiently produces 2-keto-3-deoxy-D-gluconic acid.

Then, the inventors isolated a gluconate dehydratase from bacterial cells of this strain by various purification techniques, and allowed the gluconate dehydratase to stand at 55° C. for 2 hours. As a result, it was found that the gluconate dehydratase is so heat-resistant as to maintain at least 95% of the activity.

In spite of the report that the dehydration activity of the gluconate dehydratase derived from *Alcaligenes* sp. strain M250 is 50% degraded in storage at 0° C. for 7 days in a Tris buffer (pH 8.0 to 8.8) containing 1 mM of sodium D-gluconate and 1 mM of magnesium chloride, the inventors found that the gluconate dehydratase of the present invention is so stable as to maintain the activity stably for one month under the same conditions.

In addition, while it has been reported that the molecular weight of the gluconate dehydratase purified from *Alcaligenes* sp. strain M250 determined by gel permeation chromatography is 270,000±2,500, the molecular weight of the gluconate dehydratase of the present invention is different and 188,000±2,500.

Moreover, the inventors successfully determined the amino acid sequence of the gluconate dehydratase shown in SEQ ID NO:2 of the sequence listing.

Furthermore, the inventors successfully produced a 2-keto-3-deoxyaldonic acid efficiently through preparing DNA containing the base sequence shown in SEQ ID No: 1 and a cell transformed with a plasmid containing a DNA fragment having the base sequence, preparing the gluconate dehydratase so as to be active, and reacting the corresponding aldonic acid with the transformed cell or processed product from the transformed cell. Thus, the inventors have accomplished the present invention.

According to an aspect of the present invention, a gluconate dehydratase capable of dehydrating D-gluconic acid to produce 2-keto-3-deoxy-D-gluconic acid is provided. The gluconate dehydratase maintains at least 95% of its enzyme activity after being allowed to stand in 30 mM tris(hydroxymethyl)aminomethane buffer solution with a pH of about 8.5 containing 1 mM of sodium D-gluconate and 1 mM of magnesium chloride at 55° C. for 2 hours.

Preferably, the gluconate dehydratase is derived from *Achromobacter xylosoxidans*.

The gluconate dehydratase may be defined by an amino acid sequence shown in SEQ ID NO:2.

The gluconate dehydratase may be defined by an amino acid sequence having a homology of at least 70% with the amino acid sequence shown in SEQ ID NO:2.

According to another aspect of the present invention, a gene encoding the gluconate dehydratase is provided.

The gene may be defined by a base sequence shown in SEQ ID No: 1.

According to another aspect of the present invention, a gene encoding the gluconate dehydratase is provided which is defined by a base sequence capable of hybridizing with the foregoing gene under stringent conditions.

According to another aspect of the present invention, a plasmid containing any one of the genes above is provided.

The present invention is also directed to a transformed cell prepared by transforming a host cell with the plasmid.

Preferably, the host cell is *Escherichia coli*.

The present invention is also directed to a process for converting an aldonic acid into a corresponding 2-keto-3-deoxyaldonic acid. The process includes the step of converting the aldonic acid into the 2-keto-3-deoxyaldonic acid in a water-based medium with one selected from the group consisting of the gluconate dehydratase, the transformed cell, and processed products from the gluconate dehydratase and the transformed cell.

The present invention is also directed to a process for producing a 2-deoxyaldonic acid. The process includes the steps of: reacting an aldonic acid or a salt of the aldonic acid with one selected from the group consisting of the gluconate dehydratase, the transformed cell, and processed products from the gluconate dehydratase and the transformed cell in a water-based medium to convert the aldonic acid or the salt into a 2-keto-3-deoxyaldonic acid; and reacting the 2-keto-3-deoxyaldonic acid with an oxidizing agent in a water-based medium to decarboxylate and to reduce the carbon number by 1, thereby producing the 2-deoxyaldonic acid.

The present invention is also directed to a process for producing a 2-deoxyaldose. The process includes the steps of: reacting an aldonic acid or a salt of the aldonic acid with one selected from the group consisting of the gluconate dehydratase, the transformed cell, and processed products from the gluconate dehydratase and the transformed cell in a water-based medium to convert the aldonic acid or the salt into a 2-keto-3-deoxyaldonic acid; reacting the 2-keto-3-deoxyaldonic acid with a reducing agent in a water-based medium to prepare a 2-hydroxy-3-deoxyaldonic acid; and reacting the 2-hydroxy-3-deoxyaldonic acid with an oxidizing agent in a water-based medium to decarboxylate and to reduce the carbon number by 1, thereby producing the 2-deoxyaldose.

The aldonic acid may be selected from the group consisting of D-gluconic acid, D-galactonic acid, D-fuconic acid, D-xylonic acid, and L-arabonic acid.

The gluconate dehydratase has a thermostability and a storage stability. The present invention provides a base sequence encoding the gluconate dehydratase, a plasmid containing the base sequence, and a cell transformed with the plasmid. By using the gluconate dehydratase or the transformed cell, a 2-keto-3-deoxy aldonic acid and a 2-deoxyaldonic acid or 2-deoxyaldose whose carbon number is reduced by 1 can be efficiently produced.

BRIEF DESCRIPTION OF THE DRAWINGS

The FIGURE shows the structure of a plasmid containing a DNA encoding a gluconate dehydratase gene.

DESCRIPTION OF THE PREFERRED EMBODIMENTS

The present invention will now be further described in detail.

A gluconate dehydratase of the present invention is heat-resistant, and acts on D-gluconic acid to catalyze a reaction for producing 2-keto-3-deoxy-D-gluconic acid. More specifically, the gluconate dehydratase is so heat-resistant as to maintain at least 95% of the enzyme activity to the initial activity after being allowed to stand in 30 mM Tris buffer (pH 8.5) containing 1 mM of sodium D-gluconate and 1 mM of magnesium chloride at 55° C. for 2 hours.

The gluconate dehydratase of the present invention may be derived from any type of microorganism or prepared by genetically modifying a known gluconate dehydratase, as long as it is heat resistant and has gluconic acid dehydration activity. The gluconate dehydratase may be derived from *Achromobacter xylosoxidans* strain ATCC 9220. The *Achromobacter xylosoxidans* strain ATCC 9220 can be provided from the American Type Culture Collection. This strain was referred to as *Alcaligenes xylosoxidans* or *Alcaligenes faecalis* before.

The gluconate dehydratase activity in the present invention produces 2-keto-3-deoxy-D-gluconic acid, using D-gluconic acid as the substrate. The activity can be determined as follows: A reaction mixture in an amount of 1 mL containing 1 μmmol of a Tris buffer (pH 8.5), 40 μmol of sodium D-gluconate, 1 μmol of magnesium chloride, and the gluconate dehydratase is allowed to react at 37° C. for 10 minutes, and 200 μL of 1 M hydrochloric acid solution is added to the reaction mixture to stop the reaction; and then, the amount of the resulting 2-keto-3-deoxy-D-gluconic acid is determined by high-performance liquid chromatography (column: Shodex Asahipak NH2P-50 4E, produced by Showa Denko, column temperature: 40° C., mobile phase: 50 mM sodium dihydrogen phosphate solution, flow rate: 1 mL/min, detection at 210 nm). An amount of enzyme for catalyzing the production of 1 μmol of 2-keto-3-deoxy-D-gluconic acid for one minute is defined as 1 U. The amount of protein may be determined by a dye-binding method using a Bio-Rad protein assay kit.

The gluconate dehydratase of the present invention may have an amino acid sequence shown in SEQ ID NO:2 of the sequence listing or an amino acid sequence prepared by substitution in, deletion from, modification in, insertion to, or addition to the amino acid sequence shown in SEQ ID NO:2 of at least one amino acid, preferably several amino acids, to an extent maintaining the gluconate dehydration activity. The gluconate dehydratase of the present invention may contain a protein having a homology of at least 70% with the amino acid sequence shown in SEQ ID NO:2, preferably at least 80%, and more preferably at least 95%. Protein homologies can be searched with a program, such as FASTA or BLAST, in protein amino acid sequence databases, such as SWISS-PROT and PIR, and DNA databases, such as DNA Databank of JAPAN (DDBJ), EMBL, and Gene-Bank, for example, on the Internet. The homology of at least 70% herein is a positive homology based on, for example, the BLAST program.

A polynucleotide encoding the gluconate dehydratase of the present invention contains a base sequence shown in SEQ ID No: 1. The base sequence shown in SEQ ID No: 1 in the sequence listing encodes a protein shown in SEQ ID NO:2. The base sequence encoding the amino acid sequence shown in SEQ ID NO:2 contains not only the base sequence shown in SEQ ID No: 1, but also any base sequence based on different codons. Homologues of the polynucleotide can be prepared by appropriate substitution, deletion, insertion, or addition. The homologues of the polynucleotide are prepared by substitution in, deletion from, or addition to the base sequence shown in SEQ ID No: 1 to an extent maintaining a predetermined enzyme activity of the gluconate dehydratase which is encoded by the homologues. The homologues include a polynucleotide having a base sequence capable of hybridizing under stringent conditions with a polypeptide having a base sequence complementary to the base sequence shown in SEQ ID No: 1.

Stringent hybridization may be performed according to the method described in Molecular Cloning, Cold Spring Harbor Laboratory Press; or Current Protocols in Molecular Biology, Wiley Interscience. A commercially available system, such as Gene Image System of Amersham Biosciences may also be used. Specifically, hybridization is performed as follows. A DNA or RNA molecule of a test sample transferred onto a film is hybridized with a probe labeled according to a product protocol in a hybridization buffer designated by the protocol. The hybridization buffer contains 0.1 percent by weight of SDS, 5 percent by weight of dextran sulfate, 1/20 by volume of blocking agent supplied with the kit, and 2 to 7×SSC. For the hybridization agent, a preparation having a concentration of 5 times that of a mixture containing 100× Denhardt's solution, 2% (w/v) Bovine serum albumin, 2% (w/v) Ficoll™ 400, and 2% (w/v) polyvinyl pyrrolidone may be diluted to 20 times. Preferably, the hybridization is performed at a temperature in the range of 40 to 80° C., and more preferably 50 to 70° C. Then, after being incubated for several hours or overnight, the film is washed with a washing buffer. Washing is preferably performed at room temperature, and more preferably at the same temperature as in hybridization. The washing buffer is a solution of 6×SSC and 0.1 percent by weight of SDS, preferably 4×SSC and 0.1 percent by weight of SDS, and more preferably 1×SSC and 0.1 percent by weight of SDS. After washing with such a buffer, the DNA or RNA molecule hybridized with the probe is identified with the label used in the probe.

The DNA encoding the novel gluconate dehydratase of the present invention can be isolated by the following process, for example. Genome DNA is purified from microorganisms. After being digested by a restriction enzyme, the DNA is fractionated according to length by ultracentrifugation or electrophoresis. The fractions of the DNA are collected and inserted into plasmids to prepare a plasmid library. A clone exhibiting gluconic acid dehydration activity is selected from the library. Thus, a plasmid containing a DNA encoding the gluconate dehydratase is obtained. By analyzing the base sequence of the plasmid, the base sequence of the DNA encoding the target gluconate dehydratase is determined. Thus, the amino acid sequence of the gluconate dehydratase is estimated from the DNA base sequence.

The isolated DNA is inserted into an expression plasmid to prepare a gluconate dehydratase expression plasmid. For example, in the case where the host is *Escherichia coli*, the DNA is inserted into pUC18, pKK223-3, pBR322, pMW119, Bluescript II SK(+), pSC101, or other expression plasmid. Any type of organism may be used as the host for transformation, as long as it allows the recombination vector to grow stably and autonomously and characteristics of exogenous DNA to be expressed. A typical example of the host is *Escherichia coli*, but is not limited to this. Other examples of the host include bacteria, such as *Escherichia*, *Bacillus* including *Bacillus subtilis*, and *Pseudomonas*; yeasts, such as *Saccharomyces*, *Pichia*, and *Candida*; and mould fungi, such as *Aspergillus*.

In the present invention, cells transformed with the plasmid may be cultured according to known information to produce the gluconate dehydratase of the present invention. For the cultivation, any culture medium containing adequate amounts of a carbon source, a nitrogen source, and inorganic and other nutrients may be used whether a synthetic medium or a natural medium. The cultivation is performed in a culture broth containing the above-mentioned nutrients by a conventional method, such as shake culture, aeration and spinner culture, continuous culture, or fed batch culture. Cultivation conditions are appropriately selected according to the type of culture medium and cultivation method, and are not particularly limited as long as the strain grows to produce the gluconate dehydratase.

In the process for preparing a 2-keto-3-deoxyaldonic acid, the gluconate dehydratase may be in a form of culture broth containing bacterial cells having gluconate dehydratase activity, of transformed cell prepared from the culture broth by centrifugation and collection, or of processed product from the transformed cell. Such processed products include an extract from or a fragmentized product of the transformed cell, products isolated and purified from the gluconate dehydratase-active fraction of the extract or fragmentized product, and immobilized products in which the transformed cell, the extract or fragmentized product, or the isolated product is immobilized on a support.

The aldonic acid used in the present invention can be prepared by a known process, and is also commercially available. Any aldonic acid capable of being converted into the corresponding 2-keto-3-deoxyaldonic acid can be used. Preferred aldonic acids include D-gluconic acid, D-galactonic acid, D-fuconic acid, D-xylonic acid, and L-arabonic acid. In addition, alkali metal salts, alkaline-earth metal salts, and amine salts of the aldonic acid may also be used.

The concentration of the aldonic acid is not particularly limited, but generally in the range of 1 to 500 g/L. Preferably, it is 100 g/L or more from the viewpoint of reactivity and cost efficiency.

The temperature of the reaction for preparing the 2-keto-3-deoxyaldonic acid is set in a range in which the gluconate dehydratase can maintain the activity, and preferably in the range of 50 to 60° C.

The pH of the reaction is set in a range in which the gluconate dehydratase can maintain the activity, and preferably in the range of 7 to 9. If the pH varies during the reaction, pH can be appropriately adjusted.

The reaction medium may be water or a water-based medium containing a buffer solution. The buffer solution contains in water, for example, at least one selected from the group consisting of phosphoric acid, Tris, citric acid, acetic acid, boric acid, glycine, 2-[4-(2-hydroxyethyl)-1-piperazinyl]ethanesulfonic acid, 3-morpholinopropanesulfonic acid, 2-morpholinoethanesulfonic acid, 3-cyclohexylaminopropanesulfonic acid, 2-(cyclohexylamino)ethanesulfonic acid, and piperazine-N,N'-bis(2-ethanesulfonic acid) and their salts.

In order to further increase the efficiency and yield of the reaction, various types of additive may be added, if necessary. Since some gluconate dehydratases are activated by, for example, magnesium or manganese ions, such a divalent metal may be added into the reaction liquid.

The process for producing a 2-deoxyaldonic acid includes the step of preparing a 2-keto-3-deoxyaldonic acid, as described above, and the step of reacting the resulting 2-keto-3-deoxyaldonic acid with an oxidizing agent to decarboxylate into a 2-deoxyaldonic acid whose carbon number is reduced by 1.

Oxidizing agents used for the decarboxylation include hypochlorous acid, hypochlorites, and hydrogen peroxide. Preferably, hypochlorous acid or a hypochlorite is used. The hypochlorite may be sodium hypochlorite, potassium hypochlorite, calcium hypochlorite, or lithium hypochlorite, or may be prepared in a reaction system containing a metal hydroxide, such as sodium hydroxide, and chlorine.

The solvent used in the decarboxylation is not particularly limited as long as it helps reaction proceed. Preferably, the solvent dissolves the raw materials and is, for example, water or acetic acid.

The decarboxylation is performed at a temperature between a temperature higher than the freezing point of the solvent and the boiling point of the solvent, and preferably in the range of 20 to 50° C.

The pH of the reaction liquid of the decarboxylation is in the range of 4 to 6, preferably 4.5 to 6. Preferably, the pH of the reaction liquid is adjusted to such a range with an acid, simultaneously with the addition of the hypochlorite solution or oxidizing agent. Exemplary acids include, but not limited to, inorganic acids, such as hydrochloric acid, sulfuric acid, and phosphoric acid; lower aliphatic carboxylic acids, such as acetic acid and formic acid.

The 2-deoxyaldonic acid may be prepared by consecutive reaction in one reaction system without isolating or purifying the 2-keto-3-deoxyaldonic acid prepared in a previous step.

The process for producing a 2-deoxyaldose includes the step of preparing a 2-keto-3-deoxyaldonic acid, as described above, the step of reacting the resulting 2-keto-3-deoxyaldonic acid with a reducing agent to prepare a 2-hydroxy-3-deoxyaldonic acid, and the step of reacting the resulting 2-hydroxy-3-deoxyaldonic acid with an oxidizing agent to decarboxylate into a 2-deoxyaldose whose carbon number is reduced by 1.

The reducing agent is not particularly limited as long as it helps the reaction proceed, and is preferably sodium borohydride. The reduction reaction may be performed by catalytic hydrogenation in the presence of a metal catalyst, such as palladium.

The solvent used in the reduction is not particularly limited as long as it helps the reduction proceed. Preferably, the solvent dissolves the raw materials and is, for example, water.

The reduction is performed at a temperature between a temperature higher than the freezing point of the solvent and the boiling point of the solvent, and preferably in the range of 0 to 20° C.

The decarboxylation may be performed under the same conditions as in the decarboxylation in the process for producing the 2-deoxyaldonic acid.

The 2-deoxyaldose may be prepared by consecutive reaction in one reaction system without isolating or purifying the reaction products prepared previous steps.

For isolation and collection of the products 2-keto-3-deoxyaldonic acid, 2-deoxyaldonic acid, and 2-deoxyaldose, a conventional method is applied. For example, the products may be precipitated in a metal salt form or subjected to column chromatography.

EXAMPLES

The present invention will be further described with reference to examples. However, the invention is not limited to the examples.

The amounts of the aldonic acid used in reaction and the resulting 2-keto-3-deoxyaldonic acid were determined by high-performance liquid chromatography (column: Shodex Asahipak NH2P-50 4E, produced by Showa Denko, column temperature: 40° C., mobile phase: 50 mM sodium dihydrogen phosphate solution, flow rate: 1 mL/min, detection at 210 nm).

Example 1

Cultivation of *Achromobacter xylosoxidans* Strain ATCC 9220:

The bacterial cells of *Achromobacter xylosoxidans* strain ATCC 9220 grown in a broth culture medium in advance were inoculated into a liquid culture medium (pH 7.0) containing 10 g/L of sodium D-gluconate, 5 g/L of yeast extract, 5 g/L of polypeptone, 3 g/L of sodium chloride, and 0.2 g/L of magnesium sulfate heptahydrate, and subjected to aeration and spinner culture at 30° C. for 20 hours. The cultured cells were collected by centrifugation to yield bacterial cells having gluconate dehydratase activity.

Example 2

Synthesis of 2-keto-3-deoxy-D-gluconic Acid with *Achromobacter xylosoxidans* Strain ATCC 9220:

In 200 mL of 50 mM Tris buffer (pH 7.0, containing 1 mM of sodium D-gluconate and 1 mM of magnesium chloride), 120 g of the wet bacterial cell of the *Achromobacter xylosoxidans* prepared in Example 1 were dispersed, and crushed with an ultrasonic cell crusher to prepare a crude enzyme liquid. The crude enzyme liquid was added to a solution of 1 µmol of sodium magnesium in 600 mL of water. After being adjusted to pH 8.5 with 6 M sodium hydroxide solution, the mixture was allowed to react at 50° C. During the reaction, the pH of the reaction mixture was adjusted to 8.5 by appropriately adding 2 M sodium hydroxide solution. After the reaction for 40 hours, there was not D-gluconic acid but 95 g of 2-keto-3-deoxy-D-gluconic acid in the reaction mixture.

After the completion of reaction, solid contents derived from the bacterial cells were removed from the reaction mixture by centrifugation, and the supernatant liquor was filtrated through an ultrafilter membrane (Biomax-10, produced by Millipore). The filtrate was passed through an ion-exchange column using Dowex 1×8 (200–400 meshes, OH form, produced by Dow Chemical) and eluted with 50 mL hydrochloric acid solution. The collected eluate was concentrated under reduced pressure, and then neutralized with a potassium hydroxide solution to yield 346.7 g of an aqueous solution containing 73.8 g of potassium 2-keto-3-deoxy-D-gluconate.

Example 3

Purification of Gluconate dehydratase Derived from *Achromobacter xylosoxidans* Strain ATCC 9220 and Determination of N-Terminus Amino Acid Sequence:

The bacterial cells obtained in Example 1 were suspended in 50 mM Tris buffer containing 1 mM of sodium D-gluconate and 1 mM of magnesium chloride (pH 7.0, referred to as the buffer in Example 3), and crushed with an ultrasonic cell crusher. The suspension was subjected to refrigerated centrifugation and the supernatant fluid of the suspension was collected to obtain a cell-free extract. Into the cell-free extract was added 1% of streptomycin sulfate, and the mixture was stirred for 30 minutes to form a precipitate. After removing the precipitate by centrifugation, ammonium sulfate was added to the supernatant and 20 to 60% saturated fraction was collected. The ammonium sulfate fraction was demineralized and concentrated through an ultrafilter membrane (Ultrafree-15 with a 100,000-molecular weight cut-off, produced by Millipore), then passed through a column DEAE-Sepharose FF (produced by Amersham Biosciences), and eluted by a linear concentration gradient between the buffer and another buffer containing 1 M of NaCl. The resulting active fraction was collected, and into which ammonium sulfate was added at a concentration of 1 M. The mixture was passed through a column Phenyl-Sepharose HP (produced by Amersham Biosciences) and thus eluted by a linear concentration gradient between the buffer and another buffer containing 1 M of ammonium sulfate. The resulting active fraction was collected and passed through a column Superose 12HR (produced by Amersham Biosciences), and was thus eluted with a Tris buffer containing 0.15 M of NaCl. The active fraction was collected, and into which ammonium sulfate was added at a concentration of 0.5 M. The mixture was passed through the column Phenyl-Sepharose HP, and thus eluted by a linear concentration gradient between the buffer and another buffer containing 0.5 M of ammonium sulfate. The active fraction was collected, and into which ammonium sulfate was added at a concentration of 0.5 M. The mixture was passed through the column Phenyl-Sepharose HP, and thus eluted by a linear concentration gradient between the buffer and another buffer containing 0.5 M of ammonium sulfate. The active fraction was collected and subjected to sodium dodecyl sulfate-polyacrylamide gel electrophoresis. As a result, a single band was identified at about 60 kDa. The active fraction was dialyzed against 30 mM Tris buffer (pH 8.5) containing 1 mM of sodium D-gluconate and 1 mM of magnesium chloride to exchange the buffer. The resulting enzyme solution was used as a purified gluconate dehydratase solution. Table 1 show the purification summary.

The N-terminus amino acid sequence of the protein at about 60 kDa was analyzed, and determined to be Thr-Asp-Thr-Pro-Arg-Lys-Leu-Arg-Ser-Gln-Lys-Trp-Phe-Asp-Asp, as shown in SEQ ID NO:3 of the sequence listing.

TABLE 1

Purification of Gluconate Dehydratase

| | Total protein mg | Total activity unit | Specific activity unit/mg | Purification degree | Yield % |
|---|---|---|---|---|---|
| Cell-free extract | 1322 | 284.8 | 0.22 | 1 | 100 |
| Ammonium sulfate fractionation (20–60% sat.) | 814.1 | 160.2 | 0.20 | 0.9 | 56.3 |
| DEAE Sepharose FF | 165.5 | 43.1 | 0.26 | 1.2 | 15.1 |
| 1st Phenyl Sepharose HP | 6.9 | 17.1 | 2.49 | 11.3 | 6.0 |
| Superose 12 HR | 2.9 | 20.9 | 7.23 | 32.9 | 7.3 |
| 2nd Phenyl Sepharose HP | 1.3 | 20.3 | 15.5 | 70.5 | 7.1 |
| 3rd Phenyl Sepharose HP | 1.3 | 17.0 | 13.6 | 63.3 | 6.0 |

Example 4

Thermostability of Gluconate Dehydratase Derived from *Achromobacter xylosoxidans* Strain ATCC 9220:

Samples of the purified gluconate dehydratase solution prepared in Example 3, which was dissolved in the 30 mM Tris buffer (pH 8.5) containing 1 mM sodium D-gluconate and 1 mM magnesium chloride, were allowed to stand for 30 minutes, 2 hours, or 12 hours at 4, 20, 30, 40, 50, 55, 60, 65, or 70° C. Another sample was allowed to stand at 4° C. for 7 days and 30 days. Then, each sample subjected to heat treatment as above was reacted with 1 mL of a liquid containing 1 μmmol of Tris buffer (pH 8.5), 40 μmol of sodium D-gluconate, and 1 μmol of magnesium chloride at 37° C. After 10 minutes, 200 μL of 1 M hydrochloric acid solution was added to the reaction mixture to stop the reaction. Then, the amount of 2-keto-3-deoxy-D-gluconic acid produced was determined by high-performance liquid chromatography, and the reaction rate was calculated. The results are shown in Table 2 by relative activities to the enzyme activity before heat treatment which is represented as 100. The activity of 100% was maintained after treatment at 55° C. for 2 hours, and it is also stably maintained for 30 days at 4° C.

TABLE 2

Thermostability of Gluconate Dehydratase

| | Time | | | | |
|---|---|---|---|---|---|
| | 30 min | 2 h | 12 h | 7 day | 30 day |
| Temperature | Remaining activity (%) | | | | |
| 4° C. | 100 | 100 | 100 | 100 | 105 |
| 20° C. | 103 | — | — | — | — |

TABLE 2-continued

Thermostability of Gluconate Dehydratase

| | Time | | | | |
|---|---|---|---|---|---|
| | 30 min | 2 h | 12 h | 7 day | 30 day |
| Temperature | Remaining activity (%) | | | | |
| 30° C. | 103 | — | 90 | — | — |
| 35° C. | 107 | — | 91 | — | — |
| 40° C. | 105 | — | 90 | — | — |
| 45° C. | 109 | — | — | — | — |
| 50° C. | 103 | — | 77 | — | — |
| 55° C. | 103 | 104 | — | — | — |
| 60° C. | 85 | 51 | — | — | — |
| 65° C. | 75 | — | — | — | — |
| 70° C. | 41 | — | — | — | — |

Example 5

Determination of Internal Amino Acid Sequence of Gluconate Dehydratase Derived from *Achromobacter xylosoxidans* Strain ATCC 9220:

The purified gluconate dehydratase solution (124 μg in terms of protein) prepared in Example 3 was freeze-dried, then dissolved in 100 μL of 0.5 M Tris buffer (pH 8.4) containing 6 M of guanidine hydrochloride, and warmed at 37° C. for 15 minutes. To the solution was added 10 μL of 0.5 M Tris buffer (pH 8.4) containing 0.2 M of dithiothreitol and 6 M of guanidine hydrochloride. The solution was then warmed at 60° C. for 1 hour. To the solution was added 10 μL of 0.5 M Tris buffer (pH 8.4) containing 0.4 M of iodoacetic acid and 6 M of guanidine hydrochloride. The solution was then warmed at 37° C. for 15 minutes. The resulting solution was passed through a Quick Spin column (produced by Roche Diagnostics) filled with Sephadex G-50 equilibrated with 0.5 M ammonium hydrogen carbonate solution (pH 7.8) previously containing 8 M of urea to demineralize, and thus 400 μL of solution was obtained. To this solution was added 1 μL of 2 mg/mL V8 protease (produced by Wako Pure Chemical Industries) to allowed to react at 30° C. for 23 hours. The reaction mixture was subjected to reversed-phase high performance liquid chromatography using a column Vydac 214TP54 PROTEIN C4 (produced by Agilent) to isolate the product peptide by a concentration gradient between 0.1% trifluoroacetic acid solution and 90% acetonitrile solution containing 0.1% of trifluoroacetic acid, and a fraction of the peptide was sampled. The N-terminus amino acid sequence of the peptide was analyzed, and determined to be Ala-Arg-Ala-Ile-Val-Phe-Glu-Gly-Pro-Glu-Asp-Tyr-His-Ala-Arg, as shown in SEQ ID NO:4 of the sequence listing.

Example 6

DNA Encoding Gluconate Dehydratase from *Achromobacter xylosoxidans* Strain ATCC 9220:

Genome DNA was prepared from the bacterial cells of *Achromobacter xylosoxidans* strain ATCC 9220 prepared in Example 1 according to the method for isolation of bacterial genome DNA described in "Kiso-Kagaku Jikken-Hou 2, Chushutsu, Bunri, Seisei (Basic Chemical Experiments 2, Extraction, Separation, and Purification)", Kouichi Anan, et al., published by Maruzen Company. Polymerase chain reaction (PCR) was performed to prepare DNA fragment of about 1.2 kb, using the genome DNA as a temperate, and an oligonucleotide defined by SEQ ID NO:5 synthesized according to the N-terminus amino acid sequence determined in Example 3 and an oligonucleotide defined by SEQ ID NO:6 synthesized according to the internal amino acid sequence determined in Example 5 as primer. The genome DNA was digested with typical restriction enzymes, and totally southern-hybridized with a probe prepared by labeling the DNA fragment of about 1.2 kb. As a result, when the genome DNA was completely digested with a restriction enzyme Pst I, a positive signal was found in a fragment of about 4 kb. The DNA fragments obtained by completely digesting the genome DNA with the restriction enzyme Pst I were subjected to concentration gradient ultracentrifugation to fractionate according to length, and a fraction mainly containing 4-kb DNA fragments was collected. The fraction was subjected to DNA ligation with a vector pUC118 whose 5'-terminus was dephosphorylated by digesting with the restriction enzyme Pst I to prepare a plasmid library. A transformant into which *Escherichia coli* DH5α was transformed with the plasmid library was applied onto a LB (Luria-Bertani) agarose medium containing 50 µg/mL of Ampicillin and static-cultured to produce colonies. Colony hybridization was performed with the labeled probe of 1.2-kb DNA fragment, and a colony exhibiting a positive signal was isolated. A plasmid was collected from the positive colony, and the base sequence of the resulting plasmid was analyzed. For the analysis of the base sequence, BigDye Teminator Cycle Sequencing kit and Genetic Analyzer 310, produced by Applied Biosystems, were used. According to base sequence information, two types of primer, oligonucleotides shown in SEQ ID NOS:7 and 8, were designed. The primer of SEQ ID NO:7 was provided with a restriction enzyme HindIII site; the primer of SEQ ID NO:8, restriction enzyme XbaI site. PCR was performed to expand the region containing the DNA encoding the gluconate dehydratase, using the genome DNA as the template. The PCR product was subjected to agarose gel electrophoresis and a band having a targeted mobility was cut out. Thus, the DNA was extracted from the gel with Qiaqick produced by Qiagen. The extract was subjected to DNA ligation with a vector pMW119 whose 5'-terminus was dephosphorylated by digesting with the restriction enzymes HindIII and XbaI to yield a plasmid containing the DNA encoding the gluconate dehydratase.

Example 7

Determination of DNA Encoding Gluconate Dehydratase Gene:

According to an examination, it was found that plasmid prepared in Example 6 has a physical map as shown in the FIGURE. Also, the base sequence of the plasmid was analyzed. For the determination of the base sequence, Big-Dye Teminator Cycle Sequencing kit and Genetic Analyzer 310, produced by Applied Biosystems, were used. As a result, the entire base sequence of the DNA encoding the gluconate dehydratase gene, shown in SEQ ID No: 1 was obtained. The base sequence of the gluconate dehydratase gene was translated into an amino acid sequence, and the result is shown in SEQ ID NO:2. The amino acid sequence of its N-terminus was in agreement with that of the N-terminus described in Example 3.

Example 8

Synthesis of 2-keto-3-deoxy-D-gluconic Acid with *Escherichia coli* Transformed with DNA Containing the Gene of Gluconate Dehydratase Derived from *Achromobacter xylosoxidans* Strain ATCC 9220:

*Escherichia coli* K-12 W3110 transformed with the plasmid of Example 7, shown in the FIGURE, was shake-cultured in a LB liquid medium containing 50 µg/mL of Ampicillin at 37° C. overnight. After the cultivation, bacterial cells were collected by centrifugation. Then, 50.0 g of reaction mixture was allowed to react at 50° C. which contained 0.3 g of the resulting wet bacterial cells, 6.0 g of sodium D-gluconate, 50 µmol of magnesium chloride, and 2.5 µmmol of Tris buffer (pH 8.5). After the reaction for 24 hours, there was not D-gluconic acid but 4.8 g of 2-keto-3-deoxy-D-gluconic acid in the reaction mixture.

Example 9

Synthesis of 2-keto-3-deoxy-D-galactonic Acid with *Escherichia coli* Transformed with DNA Containing the Gene of Gluconate Dehydratase Derived from *Achromobacter xylosoxidans* Strain ATCC 9220:

*Escherichia coli* K-12 W3110 transformed with the plasmid of Example 7, shown in the FIGURE, was shake-cultured in a LB liquid medium containing 50 µg/mL of Ampicillin at 37° C. overnight. After the cultivation, bacterial cells were collected by centrifugation. Then, 50.0 g of reaction mixture was allowed to react at 50° C. which contained 0.6 g of the resulting wet bacterial cells, 6.0 g of sodium D-galactonate, 50 µmol of magnesium chloride, and 2.5 µmmol of Tris buffer (pH 8.5). After the reaction for 24 hours, there was not D-galactonic acid but 4.5 g of 2-keto-3-deoxy-D-galactonic in the reaction mixture.

Example 10

Synthesis of 2-keto-3-deoxy-D-xylonic Acid with *Escherichia coli* Transformed with DNA Containing the Gene of Gluconate Dehydratase Derived from *Achromobacter xylosoxidans* Strain ATCC 9220:

*Escherichia coli* K-12 W3110 transformed with the plasmid of Example 7, shown in the FIGURE, was shake-cultured in a LB liquid medium containing 50 µg/mL of Ampicillin at 37° C. overnight. After the cultivation, bacterial cells were collected by centrifugation. Then, 110.0 g of reaction mixture was allowed to react at 50° C. which contained 0.7 g of the resulting wet bacterial cells, 13.0 g of ammonium D-xylonate, 50 µmol of magnesium chloride, and 5.5 µmmol of Tris buffer (pH 8.5). After the reaction for 24 hours, there was not D-xylonic acid but 9.9 g of 2-keto-3-deoxy-D-xylonic acid in the reaction mixture.

Example 11

Synthesis of 2-keto-3-deoxy-L-arabonic Acid with *Escherichia coli* Transformed with DNA Containing the Gene of Gluconate Dehydratase Derived from *Achromobacter xylosoxidans* Strain ATCC 9220:

*Escherichia coli* K-12 W3110 transformed with the plasmid of Example 7, shown in the FIGURE, was shake-cultured in a LB liquid medium containing 50 µg/mL of Ampicillin at 37° C. overnight. After the cultivation, bacterial cells were collected by centrifugation. Then, 10.0 g of reaction mixture was allowed to react at 50° C. which contained 0.7 g of the resulting wet bacterial cells, 1.0 g of sodium L-arabonate, 10 µmol of magnesium chloride, and 500 µmol of Tris buffer (pH 8.5). After the reaction for 24 hours, there was not L-arabonic acid but 0.7 g of 2-keto-3-deoxy-L-arabonic acid in the reaction mixture.

Example 12

Synthesis of 2-deoxyribose with Sodium Gluconate as Aldonate:

*Escherichia coli* K-12 W3110 transformed with the plasmid of Example 7, shown in the FIGURE, was shake-cultured in a LB liquid medium containing 50 µg/mL of Ampicillin at 37° C. overnight. After the cultivation, bacterial cells were collected by centrifugation. Then, 3.3 g of the resulting wet bacterial cell was added to 400 g of reaction mixture which contained 130 g of sodium D-gluconate and 10 µmol of magnesium chloride and whose pH was adjusted to 8.5 with sodium hydroxide, and allowed to react at 40° C. After the reaction for 24 hours, there was not D-gluconic acid but 106 g of 2-keto-3-deoxy-D-gluconic acid in the reaction mixture.

The resulting reaction mixture, which contained 2-keto-3-deoxy-D-gluconic acid, was cooled to 10° C. while being stirred, and 6.0 g of sodium borohydride was slowly added to the mixture with care to avoid bubbling. Then, the reaction was continued at 10° C. for 2 hours. Consequently, 100 g of 2-hydroxy-3-deoxy-D gluconic acid was produced in the reaction mixture.

The pH of the resulting reaction mixture containing the 2-hydroxy-3-deoxy-D-gluconic acid was adjusted to 5.0 with 35% hydrochloric acid solution. Into the reaction mixture was dripped 377 g of 13% sodium hypochlorite solution to perform decarboxylation over a period of 1 hour with the reaction temperature adjusted to 35° C. The pH of the reaction mixture at this time was adjusted between 5 and 6 with acetic acid. After adding the sodium hypochlorite solution, the reaction was carried out for 1 hour to yield 69 g of 2-deoxy-D-ribose. The yield from sodium D-gluconate was 86.3%.

Example 13

Synthesis of Mixture of 2-deoxy-D-ribonolactone and Sodium 2-deoxy-D-ribonate Using Sodium Gluconate as Aldonate:

*Escherichia coli* K-12 W3110 transformed with the plasmid of Example 7, shown in the FIGURE, was shake-cultured in a LB liquid medium containing 50 µg/mL of Ampicillin at 37° C. overnight. After the cultivation, bacterial cells were collected by centrifugation. Then, 3.3 g of the resulting wet bacterial cell was added to 530 g of reaction mixture which contained 130 g of sodium D-gluconate and 10 µmol of magnesium chloride and whose pH was adjusted to 8.5 with sodium hydroxide, and allowed to react at 40° C. After the reaction for 24 hours, there was not D-gluconic acid but 106 g of 2-keto-3-deoxy-D-gluconic acid in the reaction mixture.

The pH of the 2-keto-3-deoxy-D-gluconic acid solution was adjusted to 9.0 with 30% sodium hydroxide, and then to 5.0 with concentrated hydrochloric acid. While the pH was adjusted between 4.5 and 5.0 with concentrated hydrochloric acid under water-cooling, 473 g of sodium hypochlorite solution (12.2 percent by weight) was dripped over a period of 1 hour. After the completion of reaction, sodium hydrogencarbonate was added to adjust the pH to 8.0. The resulting reaction mixture was concentrated under reduced pressure at 50° C. Methanol was added to the residue and the resulting inorganic salt was removed by filtration. This step was repeated two times. The solvent of the filtrate was removed by concentration to yield 106 g of a mixture of 2-deoxy-D-ribonolactone and sodium 2-deoxy-D-ribonate. In 27 g of water was dissolved 2.7 g of the resulting mixture. After being demineralized through a cation exchange resin (Amberlite IR-120 plus), the solution was adjusted to pH 0.9 with 12 N HCl and stirred at room temperature for 12 hours. The resulting reaction solution was concentrated under reduced pressure, and then purified by silica gel column chromatography (eluant composition: chloroform/methanol=10/1 to 5/1) to yield 2.0 g of 2-deoxy-D-ribonolactone syrup quantitatively.

Example 14

Synthesis of Sodium 3,4-dihydroxybutanate with Sodium Xylonate as Aldonate:

*Escherichia coli* K-12 W3110 transformed with the plasmid of Example 7, shown in the FIGURE, was shake-cultured in a LB liquid medium containing 50 µg/mL of Ampicillin at 37° C. overnight. After the cultivation, bacterial cells were collected by centrifugation. Then, 0.5 g of the resulting wet bacterial cell was added to 53 g of reaction mixture which contained 13 g of sodium D-xylonate and 10 µmol of magnesium chloride and whose pH was adjusted to 8.5 with sodium hydroxide, and allowed to react at 40° C. After the reaction for 24 hours, there was not D-xylonic acid but 9.8 g of 2-keto-3-deoxy-D-xylonic acid in the reaction mixture.

The pH of the 2-keto-3-deoxy-D-xylonic acid solution was adjusted to 5.0 with concentrated hydrochloric acid. While the pH was adjusted between 4.5 and 5.0 with concentrated hydrochloric acid under water-cooling, 53 g of sodium hypochlorite solution (12.2 percent by weight) was dripped over a period of 1 hour. After the completion of reaction, sodium hydrogencarbonate was added to adjust the pH to 8.0. The resulting reaction mixture was concentrated under reduced pressure at 50° C. Methanol was added to the residue and the resulting inorganic salt was removed by filtration. This step was repeated two times. The solvent of the filtrate was removed by concentration to yield 9.4 g of sodium 3,4-dihydroxybutanate.

What is claimed is:

1. An isolated gluconate dehydratase capable of dehydrating D-gluconic acid to produce 2-keto-3-deoxy-D-gluconic acid, the gluconate dehydratase maintaining at least 95% of the enzyme activity thereof after being allowed to stand in 30 mM tris(hydroxymethyl)aminomethane buffer solution with a pH of about 8.5 containing 1 mM of sodium D-gluconate and 1 mM of magnesium chloride at 55° C. for 2 hours; wherein the gluconate dehydratase is defined by the amino acid sequence shown in SEQ ID No: 2.

2. The isolated gluconate dehydratase according to claim 1, wherein the gluconate dehydratase is derived from *Achromobacter xylosoxidans*.

* * * * *